United States Patent
Yao et al.

(10) Patent No.: US 11,484,198 B2
(45) Date of Patent: Nov. 1, 2022

(54) MINIATURIZED INDIRECT OPHTHALMOSCOPY FOR WIDE-FIELD FUNDUS PHOTOGRAPHY

(71) Applicant: THE BOARD OF TRUSTEES OF THE UNIVERSITY OF ILLINOIS, Urbana, IL (US)

(72) Inventors: Xincheng Yao, Hinsdale, IL (US); Devrim Toslak, Konyaalti/Antalya (TR)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 341 days.

(21) Appl. No.: 16/639,697

(22) PCT Filed: Aug. 17, 2018

(86) PCT No.: PCT/US2018/000273
§ 371 (c)(1),
(2) Date: Feb. 17, 2020

(87) PCT Pub. No.: WO2019/035992
PCT Pub. Date: Feb. 21, 2019

(65) Prior Publication Data
US 2020/0237212 A1 Jul. 30, 2020

Related U.S. Application Data
(60) Provisional application No. 62/546,830, filed on Aug. 17, 2017.

(51) Int. Cl.
*A61B 3/12* (2006.01)
*A61B 3/14* (2006.01)

(52) U.S. Cl.
CPC ............ *A61B 3/12* (2013.01); *A61B 3/145* (2013.01)

(58) Field of Classification Search
CPC ............ A61B 3/10; A61B 3/12; A61B 3/145
See application file for complete search history.

(56) References Cited

U.S. PATENT DOCUMENTS

2016/0296112 A1  10/2016 Fletcher et al.
2016/0338587 A1  11/2016 Gupta

OTHER PUBLICATIONS

International Search Report and Written Opinion dated Jan. 29, 2019 for PCT Patent Application PCT/US2018/000273.

*Primary Examiner* — Jack Dinh
(74) *Attorney, Agent, or Firm* — Thomas | Horstemeyer, LLP

(57) ABSTRACT

A wide-field fundus indirect ophthalmoscopy method and apparatus are provided that can be miniaturized to be suitable for employment in a smartphone and that overcome limitations of existing smartphone wide field fundus imaging devices and methods, such as high cost, clinical deployment challenges and limited field of view. The wide-field fundus indirect ophthalmoscopy method and apparatus are also well suited for use in rural and underserved areas where both expensive instruments and skilled operators are typically not available. The wide-field fundus indirect ophthalmoscopy method and apparatus enable wide-field snapshot fundus images to be captured with wide fields of view (FOV) under mydriatic and non-mydriatic conditions and also enables video recordings of the fundus to be captured from which montages can be constructed with even wider FOVs.

18 Claims, 9 Drawing Sheets

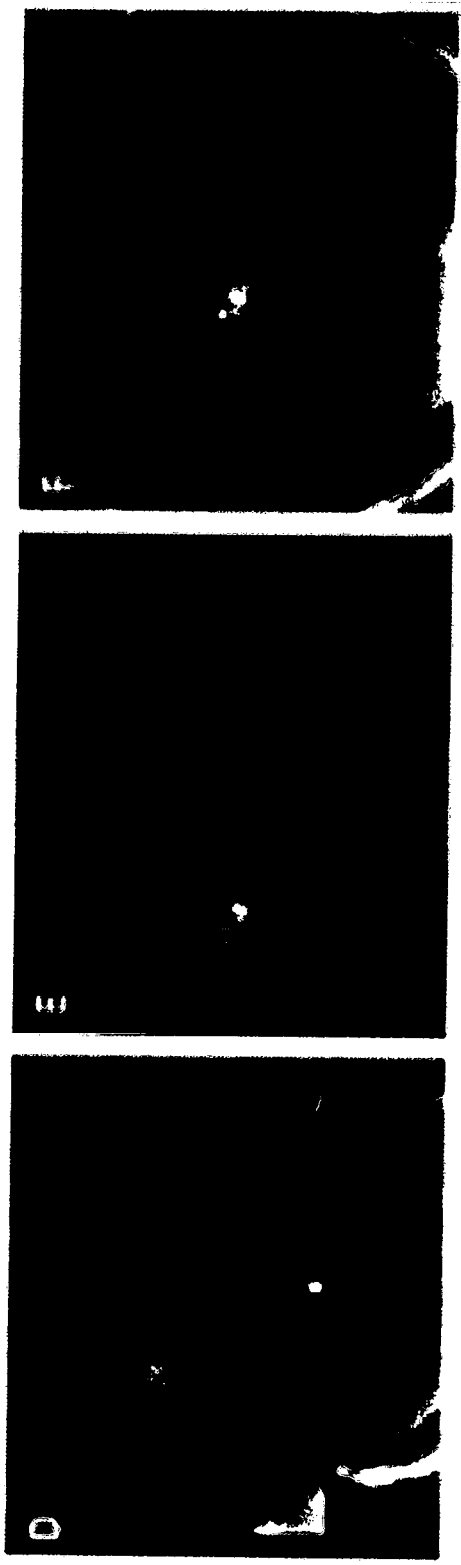

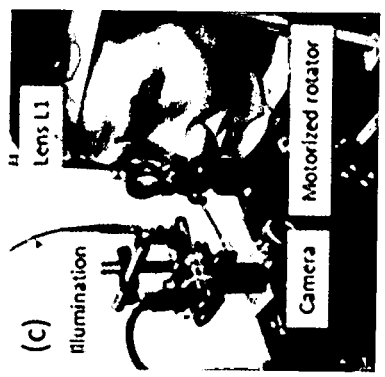
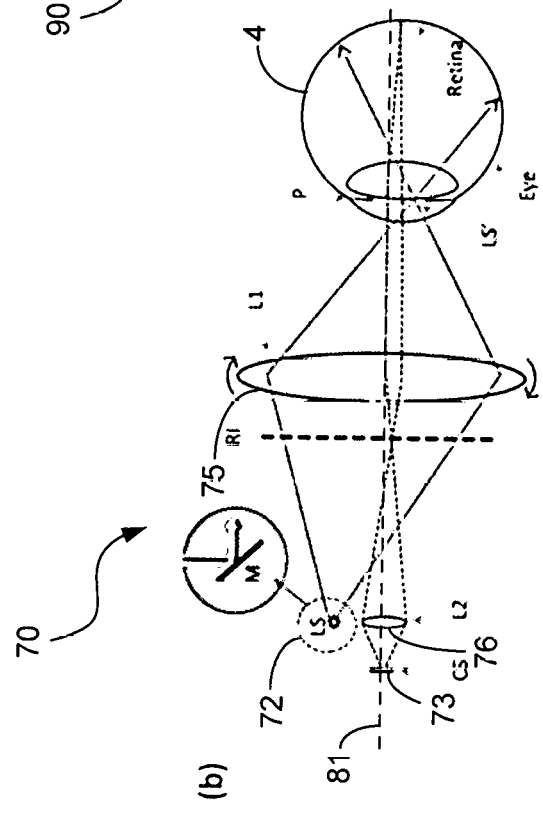
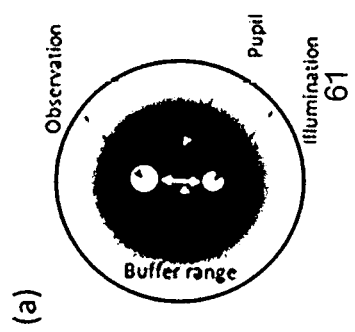
FIG. 5C
FIG. 5B
FIG. 5A

MINIATURIZED INDIRECT OPHTHALMOSCOPY FOR WIDE-FIELD FUNDUS PHOTOGRAPHY

CROSS-REFERENCE TO RELATED APPLICATIONS

The present application is a national stage entry pursuant to 35 U.S.C. § 371 of International Application No. PCT/2018/000273, filed on Aug. 17, 2018, which claims the benefit of and priority to U.S. Provisional Application No. 62/546,830, filed on Aug. 17, 2017 and entitled "MINIATURIZED INDIRECT OPHTHALMOSCOPY FOR WIDE-FIELD FUNDUS PHOTOGRAPHY", which are hereby incorporated by reference herein in their entireties.

GOVERNMENT SUPPORT

This invention was made with Government support under Contract/Grant Nos. R01 EY023522, R01 EY024628 and R21 EY025760 awarded by the National Institutes of Health. The Government has certain rights in this invention.

TECHNICAL FIELD OF THE INVENTION

This invention relates to fundus photography and retinal examination, and in particular, to a wide-field fundus camera based on a unique design of miniaturized indirect ophthalmoscopy that allows for both snapshot fundus photography and video recording of the fundus.

BACKGROUND OF THE INVENTION

Fundus examination is important for retinal disease screening, diagnosis, and treatment evaluation. However, the high equipment cost of existing devices is a limiting factor for clinical deployment of wide-field fundus photography, particularly in rural and underserved areas where both expensive instruments and skilled operators are not available. In coordination with widely available internet technology, digital fundus photography has gained increasing interest for telemedicine examination of retinal diseases.

Various smartphone-based ocular imaging techniques have been demonstrated in recent years. Low-cost smartphone fundus cameras have been developed to explore affordable telemedicine applications of diabetic retinopathy (DR), age-related macular degeneration (AMD), retinopathy of premature (ROP), etc. Low cost smartphone fundus cameras promise convenient assessment of eye diseases at point-of-care environments, and may also enable affordable telemedicine screening to foster the access to medical cares in rural and underserved areas. However, existing smartphone fundus cameras are limited by the small FOV in single-shot images. Most of these smartphone fundus cameras employ the configuration of indirect ophthalmoscopy. By directly adopting binocular indirect ophthalmoscopy (BIO) lenses, these smartphone fundus cameras provide a low-cost solution for retinal examination. However, the BIO lenses are specially designed for head mounted BIO systems, which require long distance from the lens to the smartphone camera. Therefore, the BIO lens based smartphone fundus cameras are bulky, with a small field of view (FOV), typically less than about 45° in single-shot images.

A smartphone-based fundus camera that uses a donut-shaped trans-pupillary illumination of the type used in traditional fundus cameras has been also developed. The camera combines a crossed polarization technique with flashing light. However, the FOV in single-shot images were still limited at about 55°. Moreover, the flashing light illumination excludes the potential of continuous video recording.

By employing an ophthalmoscopy technique known as trans-palpebral illumination in combination with a smartphone, an FOV of about 152° has been achieved in single-shot fundus image. However, clinical deployments of the trans-palpebral illumination-based device is challenging due to the requirement of separate adjustment and optimization of imaging and illumination sub-systems.

A need exists for a wide-field fundus indirect ophthalmoscopy method and apparatus that can be miniaturized to be suitable for employment in a smartphone and that overcome the aforementioned limitations of existing smartphone wide field fundus imaging devices and methods, such as high cost of implementation, clinical deployment challenges and limited FOV. A need also exists for a wide-field fundus indirect ophthalmoscopy method and apparatus that are well suited for use in rural and underserved areas where both expensive instruments and skilled operators are not available.

BRIEF DESCRIPTION OF THE DRAWINGS

FIG. 3D illustrates a montage of the single-shot images shown in FIGS. 3A-3C.

FIG. 3E illustrates a representative fundus image from the same subject used in FIGS. 3A-3D collected with a clinical fundus camera (Zeiss, Cirrus Photo 800), which has a single-shot FOV of 45° external angle, corresponding to 67.5° internal angle.

FIG. 3F shows the overlap of images shown in FIG. 3C and FIG. 3E for FOV comparison.

FIG. 5A illustrates the illumination strategy of a non-mydriatic miniaturized indirect ophthalmoscopy apparatus in accordance with a representative embodiment.

FIG. 5B illustrates a schematic diagram of an optical layout of the non-mydriatic miniaturized indirect ophthalmoscopy apparatus that uses the illumination strategy shown in FIG. 5A in accordance with a representative embodiment.

FIG. 5C shows a photograph of a benchtop prototype fundus camera based on the miniaturized indirect ophthalmoscopy apparatus having the optical layout shown in FIG. 5B.

DETAILED DESCRIPTION OF AN ILLUSTRATIVE EMBODIMENT

Figure 1B:
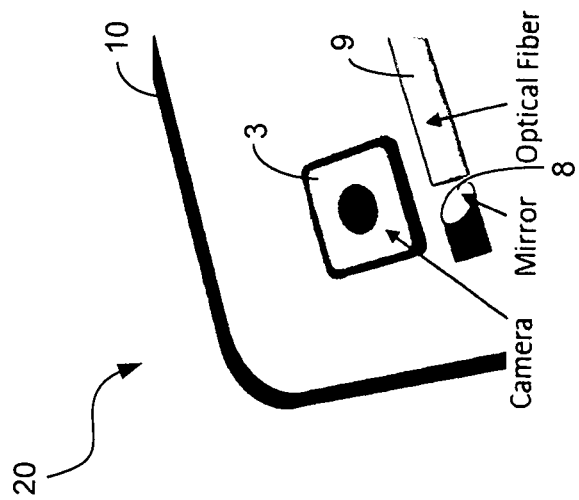
FIG. 1B is a bottom perspective view of a portion of a smartphone wide-field fundus camera having the optical layout shown in FIG. 1A in accordance with a representative embodiment.

Illustrative embodiments are disclosed herein of a wide-field fundus indirect ophthalmoscopy method and apparatus that can be miniaturized to be suitable for employment in a smartphone and that overcome the aforementioned limiting factors of existing smartphone wide field fundus imaging devices and methods, such as high cost, clinical deployment challenges and limited FOV. The wide-field fundus indirect ophthalmoscopy method and apparatus are also well suited for use in rural and underserved areas where both expensive instruments and skilled operators are not available. The wide-field fundus indirect ophthalmoscopy method and apparatus enable wide-field snapshot fundus images to be captured with wide fields of view (FOV) under mydriatic and non-mydriatic conditions and also enables video recordings of the fundus to be captured from which montages can be constructed with even wider FOVs.

In accordance with a first aspect of the inventive principles and concepts, the miniaturized wide-field fundus indirect ophthalmoscopy apparatus comprises a camera sensor, an illumination sub-system and an imaging sub-system. The illumination sub-system includes at least a first lens and a light source. The light source is positioned at least partially within a first plane and produces light of at least a first wavelength range, the first wavelength range including light of at least a first wavelength. The first lens and the light source are positioned relative to one another such that light produced by the light source is brought to focus by the first lens at a first location at which a plane of a pupil of an eye of a subject is expected to be located during an eye examination of the subject. The imaging sub-system includes at least the first lens and at least a second lens. The first lens and the second lens are positioned relative to one another along an optical axis of the apparatus along which the first and second lenses and the camera sensor are positioned such that the first lens forms an image of the retina of the eye at a location in between the first and second lenses and the second lens relays the image of the retina onto the camera sensor.

In accordance with a second inventive aspect, the second lens is positioned at least partially within the first plane, and the second lens and the light source are conjugated to a plane at which the plane of the pupil is expected to be located during the eye examination of the subject.

In accordance with a third inventive aspect, the imaging sub-system in accordance with one or more of the first and second inventive aspects further comprises a third lens positioned in between the camera sensor and the second lens. The second and third lenses relay the image of the retina onto the camera sensor.

In accordance with a fourth inventive aspect, the third lens and the camera sensor are a lens and a camera sensor, respectively, of a smartphone, and the apparatus further comprises an adapter configured to hold the smartphone and the apparatus in a predetermined spatial relationship relative to one another such that the camera sensor and the third lens are maintained in alignment along the optical axis of the apparatus.

In accordance with a fifth inventive aspect, the light source of the apparatus in accordance with one or more of first through fourth inventive aspect, includes at least a first light emitter that emits light of at least the first wavelength and an optical fiber having a proximal end and a distal end. The proximal end is positioned relative to the first light emitter to receive the light emitted by the first light emitter. The distal end of the optical fiber is positioned in or near the first plane.

In accordance with a sixth inventive aspect, the illumination sub-system of the apparatus of one or more of the first through fifth inventive aspects further comprises at least a first mirror having a first reflective surface positioned at least partially in the first plane. The distal end of the optical fiber is positioned near the first plane facing the first reflective surface. The first reflective surface is oriented to receive light emitted by the first light emitter passing out of the distal end of the optical fiber and to direct the received light toward the first lens.

In accordance with a seventh inventive aspect, the distance from the camera sensor to a surface of the first lens farthest from the second lens is less than or equal to about 20 centimeters (cm).

In accordance with an eighth inventive aspect, the distance from the camera sensor to a surface of the first lens that is farthest from the second lens is less than or equal to 10 cm.

In accordance with a sixth inventive aspect, the illumination sub-system of the apparatus in accordance with one or more of the first through eighth inventive aspects is configured to couple the light produced by the light source through a first area of the pupil of the eye, and the imaging sub-system is configured to receive light reflected from the retina that passes through a second area of the pupil and to form the image of the retina and to relay the image of the retina onto the camera sensor. The light passing through the first and second areas of the pupil does not overlap at the plane of the pupil.

In accordance with a tenth inventive aspect, said at least a first light emitter in accordance with one or more of fifth through ninth inventive aspects emits white light.

In accordance with an eleventh inventive aspect, said at least a first light emitter in accordance with the fifth through tenth aspects includes at least a second light emitter that emits near infrared light. The light emitted by the second light emitter is coupled into the proximal end of the optical fiber during retinal location and focusing adjustment. The light emitted by the first light emitter is coupled into the proximal end of the optical fiber during fundus imaging.

In accordance with a twelfth inventive aspect, the apparatus of one or more one of the first through eleventh inventive aspects further comprises a fixation target sub-system that includes a fixation target, a lens, a beam splitter and the first lens. The fixation target sub-system is configured to allow a human subject to control the apparatus to bring the eye of the subject into focus, and once in focus, to take a fundus snapshot or fundus video recording of the eye.

In accordance with a thirteenth inventive aspect, the apparatus of one or more one of the first through twelfth inventive aspects further comprises a mechanism configured to change the locations of the first lens and of the light source relative to one another after the apparatus has been used to capture a first snapshot fundus image of the eye of the subject and a processor. After the locations of the first lens and the light source relative to one another have been changed, the apparatus captures a second snapshot fundus image of the same eye of the same subject. The processor is configured to perform a digital compensation algorithm that processes the first and second snapshot fundus images to create a third snapshot fundus image corresponding to one of the first and second snapshot fundus images with any reflection artifacts removed.

In accordance with a fourteenth inventive aspect, the mechanism comprises a motorized rotator mechanically coupled to the first lens that can be controlled by the apparatus to rotate the first lens in a predetermined direction by a predetermined amount.

In accordance with a fifteenth inventive aspect, the apparatus in accordance with one or more of the first through fourteenth inventive aspects is capable of capturing fundus images having an external-angle FOV equal to or greater than 92° when the pupil of the eye of the subject is in a dilated state.

In accordance with a sixteenth inventive aspect, the apparatus is capable of capturing fundus images having an external-angle FOV equal to or greater than 67° when the pupil of the eye of the subject is in a non-dilated state.

In accordance with a seventeenth inventive aspect, the method for performing wide-field fundus indirect ophthalmoscopy comprises:

with a first light source of an illumination sub-system, producing light of at least a first wavelength range, the first wavelength range including light of at least a first wavelength, the first lens and the first light source being positioned relative to one another such that light produced by the first light source is brought to focus by a first lens of the illumination sub-system at a first location at which a plane of a pupil of an eye of a subject is expected to be located during an eye examination of the subject, the light source being positioned at least partially within a first plane;

with an imaging sub-system including at least the first lens and at least a second lens positioned relative to one another along an optical axis along which a camera sensor is also positioned, forming an image of a retina of the eye at a location in between the first and second lenses and relaying the image of the retina onto the camera sensor; and with the camera sensor, receiving the image of the retina and producing at least one of a snapshot fundus photograph and a video recording.

In accordance with an eighteenth inventive aspect, the second lens is positioned at least partially within the first plane, and the second lens and the first light source are conjugated to the plane at which the plane of the pupil is expected to be located during the eye examination of the subject.

In accordance with a nineteenth inventive aspect, the imaging sub-system of one or more of the seventeenth and eighteenth aspects further comprises a third lens positioned in between the camera sensor and the second lens. The second and third lenses relay the image of the retina onto the camera sensor.

In accordance with a twentieth inventive aspect, the third lens and the camera sensor are a lens and a camera sensor, respectively, of a smartphone, and the smartphone, the illumination sub-system and the imaging sub-system are mechanically coupled with an adapter that holds the smartphone and the illumination and imaging sub-systems in a predetermined spatial relationship relative to one another such that the camera sensor and the third lens are maintained in alignment along the optical axis.

In accordance with a twenty-first inventive aspect, the first light source includes at least a first light emitter that emits light of at least the first wavelength and an optical fiber having a proximal end and a distal end. The proximal end is positioned relative to the first light emitter to receive the light emitted by the first light emitter. The distal end of the optical fiber is positioned in or near the first plane.

In accordance with a twenty-second inventive aspect, the illumination sub-system of one or more of the seventeenth through twenty-first inventive aspects comprises at least a first mirror having a first reflective surface positioned at least partially in the first plane. The distal end of the optical fiber is positioned near the first plane facing the first reflective surface. The first reflective surface is oriented to receive light emitted by the first light emitter passing out of the distal end of the optical fiber and to direct the received light toward the first lens.

In accordance with a twenty-third inventive aspect, the distance from the camera sensor to a surface of the first lens that is farthest from the second lens is less than or equal to about 20 cm when performing the method.

In accordance with a twenty-fourth inventive aspect, the distance from the camera sensor to a surface of the first lens that is farthest from the second lens is less than or equal to about 10 cm when performing the method.

In accordance with a twenty-fifth inventive aspect, the illumination sub-system used in the method couples the light produced by the first light source through a first area of the pupil of the eye and the imaging sub-system receives light reflected from the retina that passes through a second area of the pupil. The light passing through the first and second areas of the pupil does not overlap.

In accordance with a twenty-sixth inventive aspect, the first light emitter used in the method emits white light.

In accordance with a twenty-seventh inventive aspect, said at least a first light emitter used in the method includes at least a second light emitter that emits near infrared light. The method further comprises:

during retinal location and focusing adjustment, emitting light from the second light emitter and coupling the light emitted by the second light emitter into the proximal end of the optical fiber; and after retinal location and focusing adjustment and during fundus imaging, emitting light from the first light emitter and coupling the light emitted by the first light emitter into the proximal end of the optical fiber.

In accordance with a twenty-eighth inventive aspect, the method further comprises:

with the camera sensor, capturing a first snapshot fundus image of the eye of the subject;

with a mechanism mechanically coupled to the first lens, changing the locations of the first lens and of the light source relative to one another;

with the camera sensor, capturing a second snapshot fundus image of the same eye of the same subject; and with a processor configured to perform a digital compensation algorithm, processing the first and second snapshot fundus images in accordance with the digital compensation algorithm to create a third snapshot fundus image corresponding to one of the first and second snapshot fundus images with any reflection artifacts removed.

In accordance with a twenty-ninth inventive aspect, the mechanism comprises a motorized rotator mechanically coupled to the first lens that can be controlled by the processor to rotate the first lens in a predetermined direction by a predetermined amount.

In accordance with a thirtieth inventive aspect, the illumination sub-system includes at least a second light source that is positioned at least partially within the first plane a distance away from the first light source and emits light in the first wavelength range. The method further comprising:

with the camera sensor, capturing a first snapshot fundus image of the eye of the subject from light of the first wavelength emitted by the first light source;

with the camera sensor, capturing a second snapshot fundus image of the eye of the subject from light of the first wavelength emitted by the second light source; and with a processor configured to perform a digital compensation algorithm, processing the first and second snapshot fundus images in accordance with the digital compensation algorithm to create a third snapshot fundus image corresponding to one of the first and second snapshot fundus images with any reflection artifacts removed.

In accordance with a thirtieth inventive aspect, said at least one of a snapshot fundus photograph and a video recording has an external-angle FOV equal to or greater than 92° when the pupil of the eye of the subject is in a dilated state.

In accordance with a thirty-first inventive aspect, said at least one of a snapshot fundus photograph and a video recording has an external-angle FOV equal to or greater than 67° when the pupil of the eye of the subject is in a non-dilated state.

In accordance with a thirty-second inventive aspect, the miniaturized wide-field fundus indirect ophthalmoscopy apparatus is for use with a camera sensor of a portable device. The apparatus comprises an illumination sub-system and an imaging sub-system. The illumination sub-system includes at least a first lens and a light source. The light source is positioned at least partially within a first plane and produces light of at least a first wavelength range. The first wavelength range includes light of at least a first wavelength. The first lens and the light source are positioned relative to one another such that light produced by the light source is brought to focus by the first lens at a first location at which a plane of a pupil of an eye of a subject is expected to be located during an eye examination of the subject. The imaging sub-system includes at least the first lens and at least a second lens. The first lens and the second lens are positioned relative to one another along an optical axis of the apparatus along which the first and second lenses and the camera sensor are positioned such that the first lens forms an image of a retina of the eye at a location in between the first and second lenses and the second lens relays the image of the retina onto the camera sensor.

In accordance with a thirty-fourth inventive aspect, the second lens is positioned at least partially within the first plane, and the second lens and the light source are conjugated to a plane at which the plane of the pupil is expected to be located during the eye examination of the subject.

In accordance with a thirty-fifth inventive aspect, the portable device includes a third lens that is positioned in between the camera sensor and the second lens. The second and third lenses relay the image of the retina onto the camera sensor.

In accordance with a thirty-sixth inventive aspect the apparatus further comprises an adapter configured to hold the portable device and the apparatus in a predetermined spatial relationship relative to one another such that the camera sensor and the third lens are maintained in alignment along the optical axis of the apparatus.

In accordance with a thirty-seventh inventive aspect, the portable device is a smartphone.

In the following detailed description, for purposes of explanation and not limitation, example embodiments disclosing specific details are set forth in order to provide a thorough understanding of an embodiment according to the present teachings. However, it will be apparent to one having ordinary skill in the art having the benefit of the present disclosure that other embodiments according to the present teachings that depart from the specific details disclosed herein remain within the scope of the appended claims. Moreover, descriptions of well-known apparatuses and methods may be omitted so as to not obscure the description of the example embodiments. Such methods and apparatuses are clearly within the scope of the present teachings.

The terminology used herein is for purposes of describing particular embodiments only, and is not intended to be limiting. The defined terms are in addition to the technical and scientific meanings of the defined terms as commonly understood and accepted in the technical field of the present teachings.

The term "apparatus," as that term is used herein is intended to include separate components that are provided separately and operably connected to perform the operations described herein as well as a unitary device that has a plurality of components that provided as a single unit of interconnected components, such as, for example, integrally formed components that are part of an integrally-formed, or unitary, part.

As used in the specification and appended claims, the terms "a," "an," and "the" include both singular and plural referents, unless the context clearly dictates otherwise. Thus, for example, "a device" includes one device and plural devices.

Relative terms may be used to describe the various elements' relationships to one another, as illustrated in the accompanying drawings. These relative terms are intended to encompass different orientations of the device and/or elements in addition to the orientation depicted in the drawings.

It will be understood that when an element is referred to as being "connected to" or "coupled to" or "electrically coupled to" another element, it can be directly connected or coupled, or intervening elements may be present.

The term "processor," as that term is used herein encompasses an electronic component that is able to execute a computer program or executable computer instructions. References herein to a computer comprising "a processor" should be interpreted as a computer having one or more processors or processing cores. The processor may for instance be a multi-core processor. A processor may also refer to a collection of processors within a single computer system or distributed amongst multiple computer systems. The term "computer" should also be interpreted as possibly referring to a collection or network of computers or computing devices, each comprising a processor or processors. Instructions of a computer program can be performed by multiple processors that may be within the same computer or that may be distributed across multiple computers.

Exemplary, or representative, embodiments will now be described with reference to the figures, in which like reference numerals represent like components, elements or features. It should be noted that features, elements or components in the figures are not intended to be drawn to scale, emphasis being placed instead on demonstrating inventive principles and concepts.

Figure 1A:
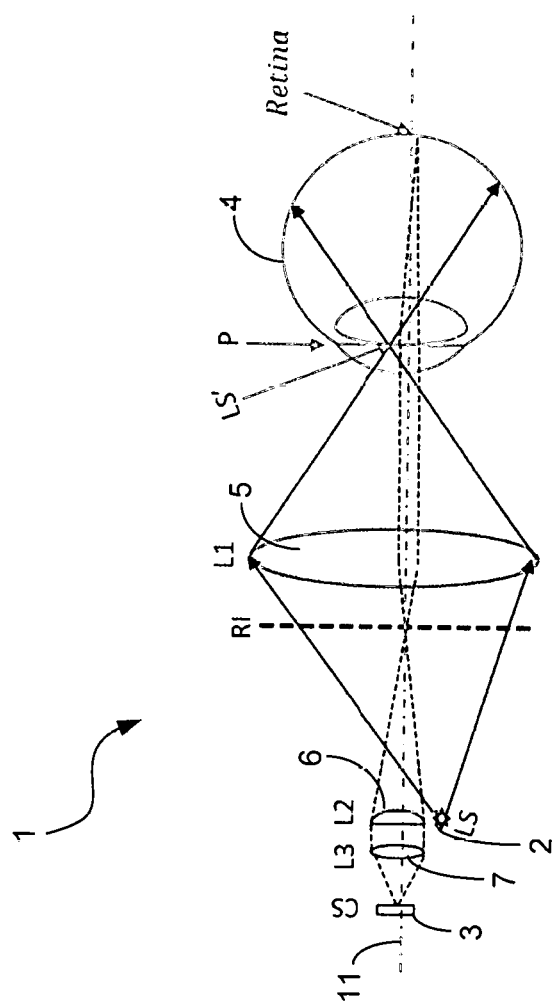
FIG. 1A illustrates the optical layout of a wide-field fundus camera in accordance with a representative embodiment capable of capturing wide-field snapshot fundus photographs and continuous video recordings.
Figures 2A, 2B:
FIGS. 2A and 2B illustrate representative photographs of back and front perspective views, respectively, of the smartphone wide-field fundus camera shown in FIG. 1B mechanically coupled to an adapter that houses optical components arranged in accordance with the optical layout shown in FIG. 1A.

FIG. 1A illustrates the optical layout 1 of the wide-field fundus indirect ophthalmoscopy apparatus in accordance with a representative embodiment capable of capturing wide-field snapshot fundus photographs and continuous video recordings. FIG. 1B is a schematic illustration of a portion of a smartphone wide-field fundus camera 10 having the optical layout 1 shown in FIG. 1A and functioning as the wide-field fundus indirect ophthalmoscopy apparatus 20 in accordance with a representative embodiment. FIGS. 2A and 2B illustrate representative photographs of back and front perspective views, respectively, of the apparatus 20 comprising the smartphone wide-field fundus camera 10 and an adapter 30 with which the camera 10 is mechanically coupled. The adapter 30 houses the lenses L1 5 and L2 6 and holds them in the optical layout shown in FIG. 1A.

With reference to FIG. 1A, a light source (LS) 2 is near a camera sensor (CS) 3 to provide illumination light for imaging the eye 4. Lens L1 5 may be, for example, a high numeric aperture (NA) lens such as a 60 diopter (D) ophthalmic lens or other high NA lens. Lens L2 6 may be, for example, a relay lens. The focal length of lens L2 6 may be, for example, 90 millimeters (mm), although other focal lengths may be used to achieve similar results, as will be understood by those of skill in the art. Lens L3 7 may be the built-in camera lens of the smartphone camera. With reference to FIG. 1B, a mirror 8 is disposed on the surface of the smartphone 10, near the CS 3 of the smartphone 10, in accordance with this representative embodiment. An optical fiber 9 is mounted on the surface of the smartphone 10 near the mirror 8.

Solid and dashed lines in FIG. 1A represent illumination light rays of the illumination light path and imaging light rays of the imaging light path, respectively. It can be seen in FIG. 1A that the illumination and imaging light paths are separated from one another in the pupil plane P and its conjugate plane in which the LS 2 and the lens L2 6 are located. The LS 2 and the lens L2 6 are located in substantially the same plane, which is perpendicular to an optical axis 11 of the optics system shown in FIG. 1A. The LS 2 preferably is as small as practicably possible, and in this embodiment, is an optical fiber. The combination of all of these features allows the apparatus to be miniaturized while still providing an extremely wide FOV. The length of the optical layout 1, or the distance along the optical axis 11 from the CS 3 to the side of lens L1 5 that is farthest from the lens L2 6 is typically less than or equal to about 20 centimeters (cm) and preferably is less than or equal to 10 cm. Thus, the apparatus 20 is based on a unique design of miniaturized indirect ophthalmoscopy. In addition, the apparatus 20 can be totally wireless and allows both snapshot fundus photography and continuous video recording.

In accordance with this representative embodiment, the CS 3 of the smartphone 10 captures single-shot images with a 92° external-angle FOV. This extremely wide FOV facilitates easy examination of retinal periphery that can be targeted by early stages of DR and other chorioretinal conditions. In coordination with widely available Internet, the continuous video mode of the apparatus 20 enables real-time, remote involvement of experienced ophthalmologists to occur, and also allows montage data processing to readily increase the effective FOV beyond 180°. In addition, the apparatus 20 is relatively easy to use and is relatively low cost, which makes it well suited for providing affordable point-of-care examination and telemedicine.

The apparatus 20 shown in FIG. 1B is designed to overcome the dimensional restrictions and cost limitations associated with constructing a totally wireless, low-weight, compact, wide-field smartphone or portable fundus camera. In accordance with this representative embodiment, which is an experimental setup, or prototype, a Samsung Galaxy S6 smartphone is used, although other smartphones and other types of portable devices may be used without departing from the inventive principles and concepts, as will be understood by those of skill in the art.

In accordance with this representative embodiment, a fiber-coupled LED 12 (FIG. 2A) powered by a battery delivers illumination light through mirror 8 (FIG. 1B), which may be a 1 mm micro mirror. The mirror 8 was conjugated to the subject pupil plane for retinal illumination. The lens L1 5 was used to image the retina through the eye, and lens L2 6, which may be, for example, a plano-convex lens with 90 mm focal length, was used to relay the retinal image to the CS 3 of the smartphone 10. Other sizes of mirrors and lenses may be used to provide similar results, as will be understood by those of skill in the art in view of the description provided herein.

The apparatus 20 and the adapter 30, which together comprise a wide-field fundus camera 40 (FIGS. 2A and 2B), has a total mass of 255 grams (g) in accordance with this representative embodiment. The fundus camera 40 allowed both snapshot fundus photography and continuous video recording as well as a 92° FOV single-shot images. Optic disc, macula, and retinal blood vasculatures can be clearly observed from the photographs and video with image quality comparable to that of a standard fundus camera. The apparatus 20 can be implemented as a low-cost, portable, wide-field smartphone fundus camera 40, which can foster clinical deployments of wide-field fundus photography for eye disease screening, diagnosis and treatment assessment. The ability of the camera 40 to perform continuous video recording creates an opportunity for remote, real-time involvement of experienced ophthalmologists.

The lens L1 5 may be a 60 D ophthalmic lens available from Volk Optical Inc., V60C, although other lenses may be used. Lens L1 5 is used to image the retina to the plane RI (dashed vertical line nearby the back focal plane of the lens L1 5 in FIG. 1A) between the lens L1 5 and lens L2 6. Lens L2 6 may be a plano-convex lens with 90 mm focal length available from Edmund Optics, 67165. The focal length of the smartphone camera lens L3 7 shown in this example embodiment is 4.3 mm, although other focal lengths may be used. The retinal image RI is relayed to the smartphone camera sensor CS 3 through the lenses L2 6 and L3 7. The Samsung Galaxy S6 smartphone used in the experimental setup, or prototype, has a 1/2.6" camera sensor with a frame resolution of 5312×2988 pixels.

The fundus camera 40 includes imaging and illumination sub-systems. With reference to FIG. 1A, the imaging sub-system comprises lens L1 5, relay lens L2 6 and the camera lens L3 7 on the smartphone 10. As indicated above, the lens L1 5 is used to image the retina to the location RI (vertical line in FIG. 1A) through the ocular lens of the subject's eye 4. In accordance with this representative embodiment, in order to achieve a wide FOV without using a single binocular indirect ophthalmoscopy (BIO) lens used in traditional indirect ophthalmoscopy systems, the relay lens L2 6 was included to overcome the space limitation of smartphone 10. The relay lens L2 6 helps to achieve the compact design of the apparatus 20 and to maximize auto-focusing capability of the built-in camera lens 3. The relay lens L2 6 is optional and may be eliminated in cases where spatial constraints are more relaxed. The relay lens L2 6, working together with built-in camera lens L3 7, relays the retinal image RI (vertical line in FIG. 1A) to the CS 3 of the smartphone 10.

The illumination sub-system includes the LS 2, which is miniaturized in accordance with this representative embodiment, and lens L1 5. Thus, lens L1 5 is a component of the imaging and illumination sub-systems. The plane of the LS 2, which is the plane in which the end face of the optical fiber lies if an optical fiber is used as the LS 2, is conjugated to subject pupil plane, P in FIG. 1A. In other words, the LS 2 is imaged to a point, LS' in FIG. 1A of the subject pupil to illuminate the posterior of the eye. As indicated above, the LS 2 and lens L2 6 are in generally the same plane, which is conjugated to the subject pupil. This parfocal configuration allows accurate illumination light delivery and confocal rejection of back reflectance of illumination light.

The illumination light rays (solid lines, FIG. 1A) reaching pupil point LS' and imaging light rays (dashed lines, FIG. 1A) reaching lens L2 6 should have no overlap at the subject pupil plane (P, FIG. 1A). This allows confocal rejection of back reflectance of illumination light.

A combination of the optical fiber 9 and mirror 8 illustrated in FIG. 1B form the LS 2. For ease of illustration, the mirror 8 is not shown in FIG. 1A. In accordance with this representative embodiment, the LS 2, in both lateral and axial directions, has small dimensions. The small dimension in the lateral direction (parallel to CS 3) helps to avoid overlap between the illumination light rays (solid lines, FIG. 1A) and imaging light rays (dashed lines, FIG. 1A) at the subject pupil plane (P, FIG. 1). The small dimension in the axial direction (parallel to optical axis 11) of the LS 2 helps the LS 2 to be located in the same plane as the aperture of the relay lens L2 6, and all illumination light can reach point LS' at the pupil plane. Otherwise, confocal rejection of back reflectance of illumination light may not work. Because of the three-dimensional (3D) structure of LEDs, directly using them as the LS in an indirect ophthalmoscopy system may not be appropriate. The 3D structure of the illuminating components can produce back reflection artefacts from the lens L1 4 (FIG. 1A). To overcome this problem, the combination of the optical fiber 9 and mirror 8 was used to form the LS 2 for the wide-field fundus camera 40 (FIGS. 2A and 2B).

In accordance with the representative embodiment shown in FIGS. 1A-2B, the single-shot, or snapshot, images and videos are captured while the subject's pupil is dilated. For capturing images and recording video, the stock camera application of the smartphone 10 was used. To capture an image, ISO was set to 100 and white-balance was set to daylight in manual imaging mode. An adjustable manual focusing slider was used for fine focusing and the screen of the smartphone 10 was filled by the retinal image by using the zoom function of the smartphone 10. A warm white LED (Thorlabs, MWWHD3) that emits white light was used as the LS 2. As indicated above, the power supply of the LED 12 was integrated into the adaptor 30 (FIGS. 2A and 2B), thereby providing a totally wireless fundus imager. The miniaturized LS 2 allows the fundus camera 10 to meet the space limitations within the smartphone 10 or other portable device. The illumination light generated by the LED 12 (FIG. 2A) was collected with a proximal end of a 1 mm diameter optical fiber 9 (FIGS. 1B and 2A), although other sizes of optical fibers may be used. As illustrated in FIG. 1B, distal end of the optical fiber 9 is optically coupled with the mirror 8, which is a 1 mm diameter, 45° aluminum coated rod lens (Edmund Optics, 47-628) in the experimental setup or prototype. The surface of the rod lens was relayed to the pupil of the subject through the lens L1 for retinal illumination.

Figures 3A, 3B, 3C:
FIGS. 3A-3C illustrate representative single-shot images captured from a forty-one-year-old subject that has no reported eye diseases.

FIGS. 3A-3C shows representative single-shot retinal images obtained by the wide-view fundus camera 40 from one normal subject without eye disease. FIG. 3D shows a montage of the three single-shot images shown in FIG. 3A-3C. FIG. 3E shows a fundus image obtained by a standard fundus camera. As shown in FIG. 3A-D, optic disc, macula, and retinal blood vasculatures can be clearly observed with image quality comparable to the fundus image shown in FIG. 3E obtained by a standard fundus camera. FIG. 3F shows the overlap of images shown in FIG. 3C and FIG. 3E for FOV comparison. It can be seen from FIG. 3F that the fundus camera 40 (FIGS. 2A and 2B) provides an even wider FOV than the standard fundus camera.

As indicated above, the fundus camera 40 also has the capability of continuous fundus video recording. To quantify the FOV and spatial resolution of the prototype fundus camera 40, the inventors took a picture of a resolution target placed at 1 m from the camera 40. By following the instructions defined by the ISO 10940:2009 standard, a 30 μm central resolution was verified, and the horizontal FOV was calculated as 62° external angle, corresponding to 92° interior angle in single-shot images. The external angle has been widely used to specify FOV in traditional fundus cameras, while interior angle is used in recently emerging wide-field fundus imagers, such as a Retcam and Optos imagers. The estimated irradiance at the retina was 0.24 mW/cm2. According to the ISO 15004-2: 2007 standard, 11.5 hours of continuous illumination is allowed for continuous video recording.

The design shown in FIG. 1 can be readily used for developing standard alone and portable fundus camera using other cameras (not necessary a smartphone camera only), and a fiber light source can be directly used as the light source for retinal illumination if there is available space to place the fiber directly, thereby obviating the need for the mirror 8.

Figure 4:
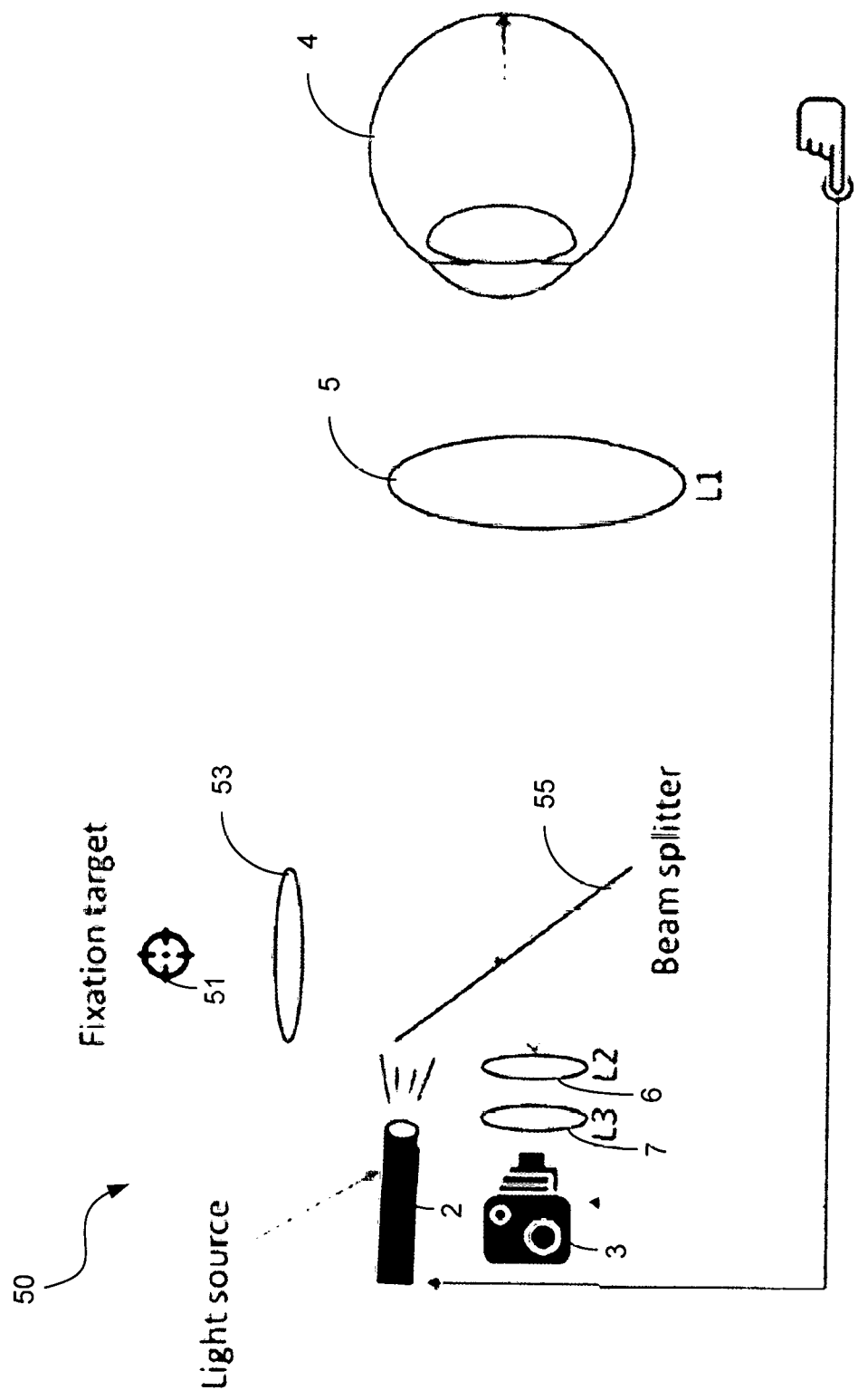
FIG. 4 is a diagram of the optical layout of a wide-field fundus camera in accordance with a representative embodiment that can function as a self-imaging system for capturing wide-field fundus images.

FIG. 4 is a diagram of the optical layout 50 of a wide-field fundus camera in accordance with a representative embodiment that can function as a self-imaging system for capturing wide-field fundus images. A fixation target 51 and the CS 3 are in substantially the same focal plane conjugated to testing the retina of the eye 4. A beam splitter 55 is reflective to light produced by the fixation target 51. A lens 53 directs light produced by the fixation target 51 onto the beam splitter 55, which reflects the light toward lens L1 5. Lens L1 5 couples the light onto the retina of the eye 4. The subject adjusts the position CS 3, typically by manually moving the smartphone (not shown) until the fixation target 51 comes into focus. Once the fixation target 51 comes into focus, the subject presses a button to take a snapshot fundus image or to start a video recording, which also activates the LS 6.

The imaging sub-system includes the lenses L1 5, L2 6 and L3 7. The illumination sub-system includes the lenses L1 5 and LS 2. The optical layout 50 also includes a fixation target subsystem that includes the fixation target 51, a lens 53, the beam splitter 55 and the lens L1 5.

The beam splitter 55 is transmissive to the light generated by the LS 2. In this embodiment, the LS 2 is an optical fiber used directly as the illumination source, i.e., without a mirror. The illumination light is coupled by lens L1 5 onto the eye 4 and the light reflected from the eye 4 is coupled by the combination of the lenses L2 2 and L3 7 onto the CS 3.

The beam splitter 55 can be replaced by a motorized flip mirror (not shown) of the type used in a DSLR camera, for example, which is flipped out of the way of the LS 2 after using the fixation target 51 for retinal imaging focus and position adjustment. Using the motorized flip mirror instead of the beam splitter 55 can improve imaging light efficiency and reduce stray light. The self-imaging function enables the feasibility of using the smartphone-based fundus camera to take fundus pictures by the patients themselves at home, promising rapid detection, easy disease progression monitoring, and low-cost treatment evaluation of DR and other eye diseases.

As indicated above, trans-pupillary illumination has been commonly employed in traditional fundus cameras. The trans-pupillary illumination typically delivers ring-shaped illumination through the periphery of the pupil, and the imaging light is collected through the central area of the pupil. In order to eliminate the corneal reflection from the retinal image, a buffer zone with enough distance between the illumination and observation zones should be provided. Otherwise, the background light due to corneal reflection will be multiple orders of magnitude stronger than the useful light back scattered/reflected from the retinal tissue, and thus overshadow the retinal image. Because only a small central pupillary area can be used for imaging purpose, and the optical system has to be sophistically optimized to guarantee that the imaged retinal area can be coincidently covered by the illumination light, the FOV of traditional fundus cameras is limited. In order to achieve the necessary view field coverage, mydriatic ETDRS 7-field photography for DR screening has been developed based on the use of the traditional fundus camera with a 30° external-angle (45° eye-angle) FOV. The 7-field photography requires a skilled operator for pupillary dilation and image registration to produce montage images. This hampers its clinical deployments in rural and underserved areas where both expensive instruments and skilled operators are not available.

A representative embodiment of a miniaturized non-mydriatic wide-field fundus indirect ophthalmoscopy method and apparatus will now be described with reference to FIGS. 5A-7D. Existing commercially available portable fundus cameras have a limited FOV, typically less than 45° external-angle (68° eye-angle), and frequently require pupillary dilation. As indicated above, trans-palpebral illumination has been employed in combination with pupillary dilation to achieve a 101° external-angle (152° eye-angle) FOV with a snapshot smartphone fundus camera. However, as also indicated above, clinical deployments of the trans-palpebral illumination-based device is challenging due to the requirement of separate adjustment and optimization of imaging and illumination sub-systems. The miniaturized indirect ophthalmoscopy-based smartphone fundus camera 40 described above with reference to FIGS. 1A-4 achieves at least a 61° external-angle (92° eye-angle) FOV, but the camera 40 is mydriatic, i.e., it is used in combination with pharmacological pupillary dilation. The following description extends the miniaturized indirect ophthalmoscopy method and apparatus to a non-mydriatic miniaturized indirect ophthalmoscopy method and apparatus.

FIG. 5A illustrates the illumination strategy of the proposed non-mydriatic miniaturized indirect ophthalmoscopy method and apparatus. Only one single spot 61 at the pupil plane is utilized for indirect ophthalmoscopy illumination. For this single-spot illumination, only a half of the pupil size is needed to provide a similar buffer range as that in ring-shape trans-pupillary illumination to eliminate the effect of cornea reflection. With pharmacological dilation, the full pupil diameter is ~8 mm. In room light condition, a 4 mm pupil diameter can be readily achieved. In dark light condition, the pupil diameter can be further enlarged without pharmacological dilation. Therefore, the miniaturized indirect ophthalmology illumination strategy allows non-mydriatic fundus photography to be achieved with a larger FOV than traditional ring-shape trans-pupillary illumination in light conditions that do not require pupil dilation.

FIG. 5B illustrates a schematic diagram of the optical layout 70 of the non-mydriatic miniaturized indirect ophthalmoscopy apparatus in accordance with a representative embodiment. The optical layout 70 is almost identical to the optical layout 1 shown in FIG. 1A, except that the light source (LS) 72 comprises both a near infrared light emitter for retinal focusing guidance and a visible light emitter for color fundus imaging. The LS 72 is near a camera sensor (CS) 73 to provide illumination light for imaging the eye 4. The optical layout 70 may be housed in and positionally arranged in an adapter that is similar or identical to the adapter 30 shown in FIGS. 2A and 2B. The CS 73 may be the CS of a smartphone, for example, such as the smartphone 10 shown in FIG. 1B.

The optical layout 70 includes an imaging sub-system and an illumination sub-system. The imaging sub-system includes lens L1 75 and lens L2 76. The illumination sub-system includes lens L1 75 and LS 72.

Solid and dashed lines in FIG. 5B represent illumination light rays of the illumination light path and imaging light rays of the imaging light path, respectively. It can be seen in FIG. 5B that the illumination and imaging light paths are separated from one another in the pupil plane P. The LS 72 and the lens L2 76 are located in substantially the same plane, which is conjugated to the pupil plane P and perpendicular to an optical axis 81 of the optics system shown in FIG. 5B. The LS 72 preferably is as small as practicably possible, and in this embodiment, is an optical fiber. The combination of all of these features allows the apparatus to be miniaturized while still providing an extremely wide FOV. The length of the optical layout 70, or the distance from the CS 73 to the side of lens L1 75 that is farthest from the lens L2 76 along the optical axis 81, is typically less than or equal to about 20 cm and preferably less than or equal to 10 cm.

FIG. 5C shows a photograph of the benchtop prototype fundus camera 90 based on the miniaturized indirect ophthalmoscopy apparatus having the optical layout 70 shown in FIG. 5B. In addition to the eye lens of the testing subject, the optical imaging system includes two optical lenses L1 75 and L2 76, the CS 73 and the LS 72. In accordance with this representative embodiment, the LS 72 and the lens L2 76 are in the substantially the same plane, with a 4 mm distance from one another, to provide enough buffer range between the illumination path and the imaging, or observation, path to prevent the effect of cornea reflection on the captured fundus image. The LS/L2 plane is conjugated to the pupil plane P (FIG. 5B). The intermediate retinal image (RI) plane is conjugated to the retina and the CS 73.

In accordance with this representative embodiment, lens L1 75 is a 40 diopter (i.e., 25 mm focal length) ophthalmic lens for imaging the retina onto the plane RI (dashed vertical line, FIG. 5B) between the lens L1 75 and lens L2 76. In accordance with this representative embodiment, the lens L2 76 is an 8 mm focal length F/2.5 micro video lens for relaying the retinal image RI to the camera sensor CS 73. In accordance with this representative embodiment, the distance between lens L1 75 and lens L2 76 is 120 mm, and the distance to the subject pupil is 31.6 mm. Considering the 25 mm focal of lens L1 75, the optical magnification from the subject pupil to the LS/L2 plane is 3.8×. Assuming the subject pupil diameter is 4 mm, the LS 72 and the lens L2 76 should be placed within a circular plane with maximum diameter 15.2 mm (4×3.8 mm). A CMOS camera (FL3-U3-120S3C-C, FLIR Integrated Imaging Solutions Inc, Richmond, Canada) was used as the CS 73 in the benchtop prototype shown in FIG. 5C. It has a frame size of 4000× 3000 pixels, with a 1.55 μm×1.55 μm pixel size and a 15 fps frame rate.

Instead of using a single visible light source as in the prototype described above with reference to FIGS. 1A-4, the LS 72 used in the non-mydriatic apparatus shown in FIG. 5C comprises two illuminators: a near infrared (central wavelength: 850 nm) LED (e.g., M850LP1, Thorlabs Inc. Newton, N.J.) for preview mode imaging, i.e., for retinal positioning and focus adjustment; and a white LED (e.g., MWWIIL4, Thorlabs Inc. Newton, N.J.) for color retinal imaging. The near infrared and white LEDs are coupled into the proximal end of one optical fiber (FIG. 5C), and the distal end of the optical fiber corresponds to the position of light source LS 72 (FIG. 5B), which is conjugated with the illumination spot, LS', within the pupil plane P (FIG. 5B).

An experiment was conducted on a human study that was approved by the Institutional Review Board of the University of Illinois at Chicago. The experiment was in compliance with the ethical standards stated in the Declaration of Helsinki.

Figures 6A, 6B, 6C:
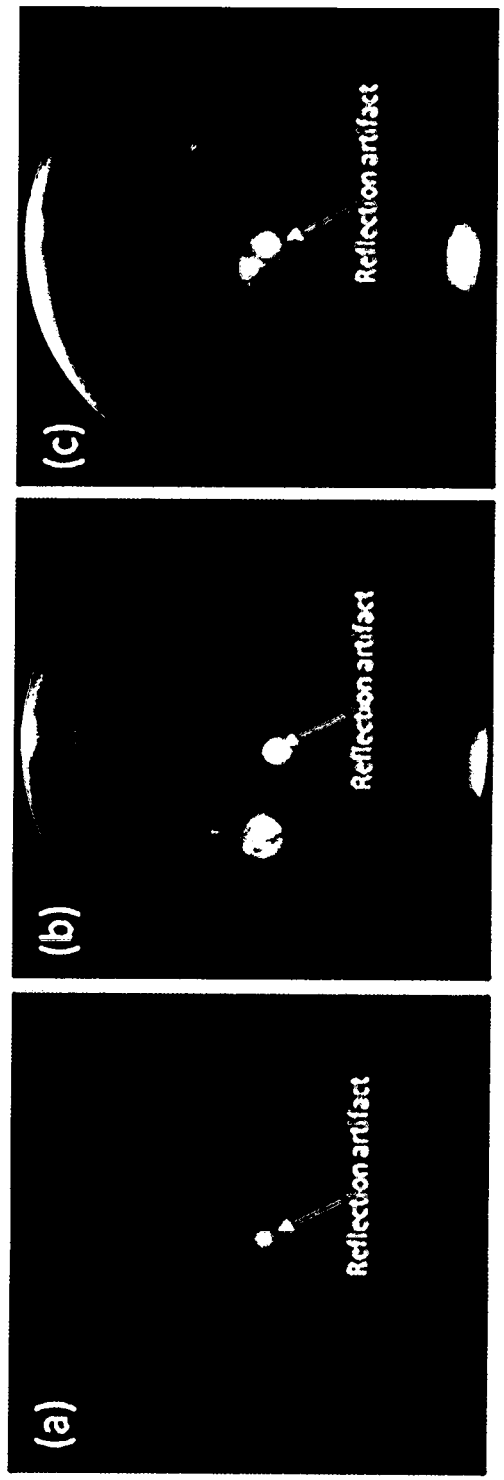
FIG. 6A shows a near infrared image captured by the prototype fundus camera shown in FIG. 5C during retinal location and focusing adjustment.
FIG. 6B shows a color fundus image captured from a Caucasian volunteer subject by the prototype fundus camera shown in FIG. 5C.
FIG. 6C shows a color fundus image captured from an Asian volunteer subject by the prototype fundus camera shown in FIG. 5C.
Figures 6D, 6E, 6F:
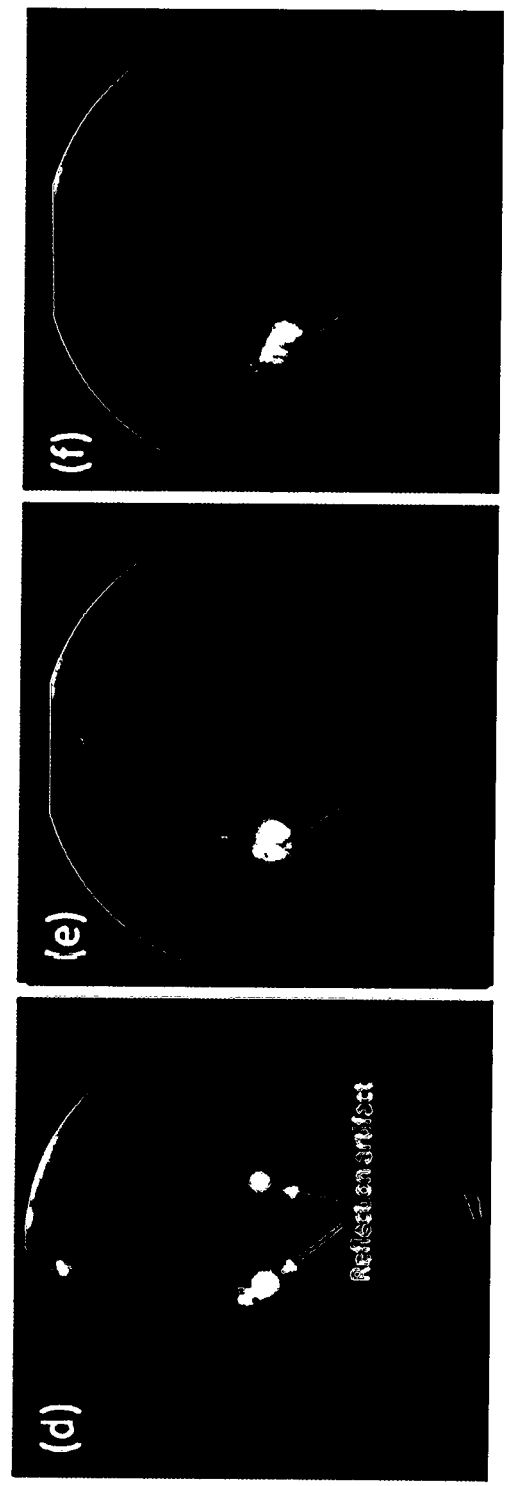
FIG. 6D shows another color fundus image captured from the same subject from which the image shown in FIG. 6B was captured by the prototype fundus camera shown in FIG. 5C after a motorized rotator was used to rotate the optical axis of the lens L1 shown in FIG. 5B to separate two reflection spots which are overlapped in the image shown in FIG. 6B.
FIG. 6E shows an artifact-free image corresponding to images shown in FIG. 6B and FIG. 6D being processed to remove the two reflection spots.
FIG. 6F provides an FOV comparison between the image shown in FIG. 6E and a color fundus image captured using a commercial fundus camera (Volk Pictor Plus) from the same subject.

FIGS. 6A-6D show representative images collected using the prototype fundus camera 80 shown in FIG. 5C. FIG. 6A shows a near infrared image captured during retinal location and focusing adjustment. FIG. 6B shows a color fundus image captured from a Caucasian volunteer subject. FIG. 6C shows a color fundus image captured from an Asian volunteer subject. FIG. 6D shows another color fundus image captured from the same subject from which the image shown in FIG. 6B was captured after a motorized rotator mechanically coupled to the lens L1 75 was used to rotate the optical axis of the lens L1 75 in the direction indicated by the arrows shown in FIG. 5B to separate two reflection spots which are overlapped in FIG. 6B. FIG. 6E shows an artifact-free image corresponding to images shown in FIG. 6B and FIG. 6D being processed to remove the reflection spots. FIG. 6F provides an FOV comparison between the image shown in FIG. 6E and a color fundus image captured using a commercial fundus camera (Volk Pictor Plus) from the same subject.

One alternative to rotating the lens L1 75 is to move the LS 72 relative to the lens L1 75 while keeping LS 72 in the same plane as lens L2 76. Any relative movement between the LS 72 and the lens L1 75 can be used for this purpose. Another alternative is to have a second LS similar or identical to LS 72 positioned in the same plane as LS 72, but spatially separated from LS 2 by a small distance. The second color fundus image would be captured from light emitted by this second LS.

According to the ISO 15004-2: 2007 standard, the weighted irradiance of the infrared and visible light were estimated as 0.06 mW/cm$^2$ and 0.22 mW/cm$^2$, respectively, at the retina. Therefore, the maximum exposure time for continuous illumination can be estimated as $t_{max}$=10 J/0.22 mW=12.6 hours.

The experiment was conducted in regular room light condition. First, the fundus camera 90 was operated with near infrared light illumination for retinal positioning and focusing adjustment. The near infrared light guidance is well suited for non-mydriatic fundus photography because it does not induce pupil constriction for relatively short exposure times, whereas direct visible light illumination can induce pupil constriction within ~300 ms. With near infrared light guidance, the inventors were able to capture at least 3 color fundus images before pupil constriction started. The inventors were aware of the slight difference between near infrared and visible light foci. In order to optimize the quality of color fundus images, the near infrared light was slightly defocused based on experimental calibration, before the white light was trigged for color fundus imaging. FIG. 6A shows a representative near infrared image captured in preview mode, i.e., during near infrared light guidance. FIGS. 6B and 6C show color fundus images from Caucasian and Asian volunteers, respectively. The exposure time was set at 50 ms. According to the ISO 10940:2009 [9], horizontal FOV was estimated as 67° external-angle (101° eye-angle), with 23 μm resolution.

Reflection artifacts were observed in FIGS. 6A, 6B, and 6C. These reelection artifacts were due to the light reflection from the surfaces of lens L1 75. While the reflection artifact is not a problem for visual evaluation performed by clinicians, it can pose a challenge for automated image analysis and classification in telemedicine applications. In principle, if two fundus images are captured, with the reflection artifacts shifted into different locations, digital compensation can be used to remove the reflection artifacts. If the fundus camera comprises a smartphone or some other portable device with digital processing capabilities, a processor of the smartphone or portable device may be configured to perform the digital compensation algorithm. Because persons of skill in the art will understand that digital compensation algorithms are known that can be used to identify and remove reflection artifacts, in the interest of brevity, the digital compensation algorithm that is used for this purpose will not be described herein in further detail.

In order to test the feasibility of performing reflection artifact removal, a motorized rotator (FIG. 5C) was used to rotate the optical axis of the lens L1 75 to capture a second retinal image, which is shown in FIG. 6D, following the acquisition of the image shown in FIG. 6B. It took~250 milliseconds to collect the two images in FIG. 6B and FIG. 6D, which is less than pupillary reaction time (~300 ms) for visible light illumination. The reflection artifacts due to the two surfaces of the lens L1 75 were overlapped together in FIG. 6B, while these two reflection spots were separated into two different locations by rotating the lens L1 in FIG. 6D. The central parts of the images of FIG. 6B and FIG. 6D were not affected significantly. With the dual-image acquisition, digital image registration and glare elimination methods were used to remove reflection artifacts. The resulting image is shown in FIG. 6E, which is essentially the same as the image shown FIG. 6B with the reflection artifact removed.

FIG. 6F is an overlapping illustration of the image shown in FIG. 6E and another fundus image captured by a commercial fundus camera (Volk Pictor Plus, Volk Optical Inc., Mentor, Ohio) from the same human subject. The Volk Pictor fundus camera provides a 45° external-angle (68° eye-angle) in a single-shot image. The comparative images further confirmed the FOV improvement of the miniaturized indirect ophthalmoscopy illumination based fundus camera 90 compared to traditional fundus camera.

Figures 7A, 7B, 7C, 7D:
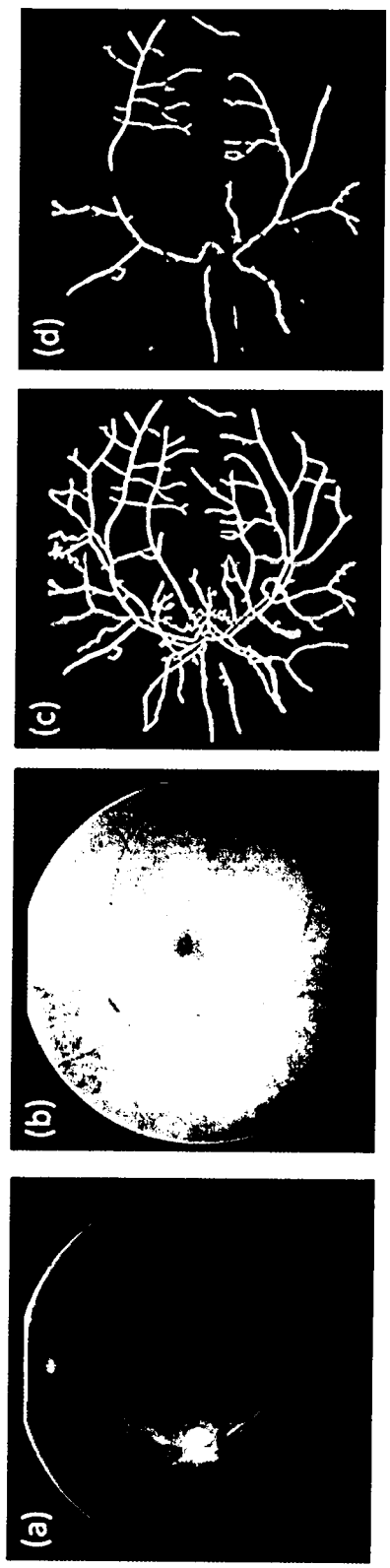
FIG. 7A shows a green-channel of the image shown in FIG. 6E.
FIG. 7B shows a red-channel of the image shown in FIG. 6E.
FIG. 7C shows a segmented blood vessel map based on the green-channel image shown in FIG. 7A.
FIG. 7D shows a differential artery-vein map based on density ratio analysis between the green-channel and red-channel images shown in FIGS. 7A and 7B, respectively.

FIGS. 7A-7D represent quantitative analysis of a representative color fundus image captured using the prototype fundus camera 90 shown in FIG. 5C. FIG. 7A shows a green-channel of the image shown in FIG. 6E. FIG. 7B shows a red-channel of the image shown in FIG. 6E. FIG. 7C shows a segmented blood vessel map based on the green-channel image shown in FIG. 7A. FIG. 7D shows a differential artery-vein map based on density ratio analysis between the green-channel and red-channel images shown in FIGS. 7A and 7B, respectively.

Quantitative analysis of fundus images is essential for objective and automated classification of eye diseases, which is particularly important for rural and underserved areas, or point-of-care environments. In order to verify the potential of using the miniaturized illumination based wide-field fundus camera 90 for quantitative image analysis, the inventors used the image shown in FIG. 6E to test automated blood vessel segmentation and artery-vein classification. As shown in FIG. 7C, individual blood vessels can be readily identified. As shown in FIG. 7D, arteries and veins can be differentiated based on optical density ratio analysis.

In summary, mydriatic and non-mydriatic miniaturized indirect ophthalmoscopy wide-field fundus cameras have been demonstrated that achieve at least a 92° external-angle FOV and a 67° external-angle FOV, respectively, in single-shot images. The fundus cameras can also be used to perform video recording of fundus images, which allows fundus image montages to be constructed that have even wider FOVs. The fundus cameras can be implemented in portable, light-weight devices, such as smartphones, for example. An NIR light can be used to guide non-mydriatic retinal imaging. True color fundus images revealed retinal structure and vasculature details. For the proof-of-concept demonstration, the benchtop prototypes were constructed using all off-the-shelf components. Dual-image acquisition combined with digital data processing has been demonstrated to achieve reflection artifact-free color fundus imaging. The apparatuses are relatively simple and low cost to construct, and can be readily packaged into portable systems, promising a next-generation low-cost and wide-field fundus camera for affordable telemedicine and point-of-care assessment of eye diseases.

It should be noted that illustrative embodiments have been described herein for the purpose of demonstrating principles and concepts of the invention. As will be understood by persons of skill in the art in view of the description provided herein, many modifications may be made to the embodiments described herein without deviating from the scope of the invention. For example, while the inventive principles and concepts have been described primarily with reference to being implemented with smartphones that can communicate wirelessly, the inventive principles and concepts are equally applicable to over types of portable and non-portable devices that can benefit from miniaturized wide-field fundus photography. Also, prototypes that used particular components were constructed to demonstrate proof of concept, but the inventive principles and concepts are not limited to the components used to build the prototypes, as will be understood by those of skill in the art in view of the description provided herein. Many modifications may be made to the embodiments described herein without deviating from the inventive principles and concepts, and all such modifications are within the scope of the invention, as will be understood by those of skill in the art.

What is claimed is:

1. A miniaturized wide-field fundus indirect ophthalmoscopy apparatus comprising:
   a camera sensor;
   an illumination sub-system including at least a first lens and a light source, the light source being positioned at least partially within a first plane and producing light of at least a first wavelength range, the first wavelength range including light of at least a first wavelength, the first lens and the light source being positioned relative to one another such that light produced by the light source is brought to focus by the first lens at a first location at which a plane of a pupil of an eye of a subject is expected to be located during an eye examination of the subject;
   an imaging sub-system including at least the first lens and at least a second lens, the first lens and the second lens being positioned relative to one another along an optical axis of the apparatus along which the first and second lenses and the camera sensor are positioned such that the first lens forms an image of a retina of the eye at a location in between the first and second lenses and said at least a second lens relays the image of the retina onto the camera sensor;
   a mechanism configured to change the locations of the first lens and of the light source relative to one another after the apparatus has been used to capture a first snapshot fundus image of the eye of the subject, wherein after the locations of the first lens and the light source relative to one another have been changed, the apparatus captures a second snapshot fundus image of the same eye of the same subject; and
   a processor configured to perform a digital compensation algorithm that processes the first and second snapshot fundus images to create a third snapshot fundus image corresponding to one of the first and second snapshot fundus images with any reflection artifacts removed.

2. The apparatus of claim 1, wherein the second lens is positioned at least partially within the first plane, and wherein the second lens and the light source are conjugated to a plane at which the plane of the pupil is expected to be located during the eye examination of the subject.

3. The apparatus of claim 1, wherein the imaging sub-system further comprises:
   a third lens positioned in between the camera sensor and the second lens, wherein the second and third lenses relay the image of the retina onto the camera sensor.

4. The apparatus of claim 3, wherein the third lens and the camera sensor are a lens and a camera sensor, respectively, of a smartphone, and wherein the apparatus further comprises:
   an adapter configured to hold the smartphone and the apparatus in a predetermined spatial relationship relative to one another such that the camera sensor and the third lens are maintained in alignment along the optical axis of the apparatus.

5. The apparatus of claim 1, wherein the light source includes at least a first light emitter that emits light of at least the first wavelength and an optical fiber having a proximal end and a distal end, the proximal end being positioned relative to the first light emitter to receive the light emitted by the first light emitter, the distal end of the optical fiber being positioned in or near the first plane.

6. The apparatus of claim 5, wherein the said at least a first light emitter emits white light.

7. The apparatus of claim 5, wherein the said at least a first light emitter includes at least a second light emitter that emits near infrared light, the light emitted by the second light emitter being coupled into the proximal end of the optical fiber during retinal location and focusing adjustment, the light emitted by the first light emitter being coupled into the proximal end of the optical fiber during fundus imaging.

8. The apparatus of claim 1, wherein the illumination sub-system further comprises:
at least a first mirror having a first reflective surface positioned at least partially in the first plane, the distal end of the optical fiber being positioned near the first plane facing the first reflective surface, the first reflective surface being oriented to receive light emitted by the first light emitter passing out of the distal end of the optical fiber and to direct the received light toward the first lens.

9. The apparatus of claim 1, wherein a distance from the camera sensor to a surface of the first lens that is farthest from the second lens is less than or equal to about 20 centimeters (cm).

10. The apparatus of claim 1, wherein a distance from the camera sensor to a surface of the first lens that is farthest from the second lens is less than or equal to 10 cm.

11. The apparatus of claim 1, wherein the illumination sub-system is configured to couple the light produced by the light source through a first area of the pupil of the eye and wherein the imaging sub-system is configured to receive light reflected from the retina that passes through a second area of the pupil, to form the image of the retina and to relay the image of the retina onto the camera sensor, wherein the light passing through the first and second areas of the pupil does not overlap at the plane of the pupil.

12. The apparatus of claim 1, further comprising:
a fixation target sub-system that includes a fixation target, a lens, a beam splitter and the first lens, the fixation target sub-system being configured to allow a human subject to control the apparatus to bring the eye of the subject into focus, and once in focus, to take a fundus snapshot or fundus video recording of the eye.

13. A method for performing wide-field fundus indirect ophthalmoscopy comprising:
with a first light source of an illumination sub-system, producing light of at least a first wavelength range, the first wavelength range including light of at least a first wavelength, a first lens and the first light source being positioned relative to one another such that light produced by the first light source is brought to focus by the first lens of the illumination sub-system at a first location at which a plane of a pupil of an eye of a subject is expected to be located during an eye examination of the subject, the light source being positioned at least partially within a first plane;
with an imaging sub-system including at least the first lens and at least a second lens positioned relative to one another along an optical axis along which a camera sensor is also positioned, forming an image of a retina of the eye at a location in between the first and second lenses and relaying the image of the retina onto the camera sensor;
with the camera sensor, receiving the image of the retina and capturing a first snapshot fundus image of the eye of the subject;
with a mechanism mechanically coupled to the first lens, changing the locations of the first lens and of the light source relative to one another;
with the camera sensor, capturing a second snapshot fundus image of the same eye of the same subject; and
with a processor configured to perform a digital compensation algorithm, processing the first and second snapshot fundus images in accordance with the digital compensation algorithm to create a third snapshot fundus image corresponding to one of the first and second snapshot fundus images with any reflection artifacts removed.

14. The method of claim 13, wherein the second lens is positioned at least partially within the first plane, and wherein the second lens and the first light source are conjugated to a plane at which the plane of the pupil is expected to be located during the eye examination of the subject.

15. The method of claim 13, wherein the first light source includes at least a first light emitter that emits light of at least the first wavelength and an optical fiber having a proximal end and a distal end, the proximal end being positioned relative to the first light emitter to receive the light emitted by the first light emitter, the distal end of the optical fiber being positioned in or near the first plane.

16. The method of claim 15, wherein said at least a first light emitter includes at least a second light emitter that emits near infrared light, the method further comprising:
during retinal location and focusing adjustment, emitting light from the second light emitter and coupling the light emitted by the second light emitter into the proximal end of the optical fiber; and
after retinal location and focusing adjustment and during fundus imaging, emitting light from the first light emitter and coupling the light emitted by the first light emitter into the proximal end of the optical fiber.

17. The method of claim 16, wherein the illumination sub-system includes at least a second light source that is positioned at least partially within the first plane a distance away from the first light source, the second light source emitting light in the first wavelength range, the method further comprising:
with the camera sensor, capturing a first snapshot fundus image of the eye of the subject from light of the first wavelength emitted by the first light source;
with the camera sensor, capturing a second snapshot fundus image of the eye of the subject from light of the first wavelength emitted by the second light source; and
with a processor configured to perform a digital compensation algorithm, processing the first and second snapshot fundus images in accordance with the digital compensation algorithm to create a third snapshot fundus image corresponding to one of the first and second snapshot fundus images with any reflection artifacts removed.

18. A miniaturized wide-field fundus indirect ophthalmoscopy apparatus for use with a camera sensor of a portable device, the apparatus comprising:
an illumination sub-system including at least a first lens and a light source, the light source being positioned at least partially within a first plane and producing light of at least a first wavelength range, the first wavelength range including light of at least a first wavelength, the first lens and the light source being positioned relative to one another such that light produced by the light source is brought to focus by the first lens at a first location at which a plane of a pupil of an eye of a subject is expected to be located during an eye examination of the subject;
an imaging sub-system including at least the first lens and at least a second lens, the first lens and the second lens being positioned relative to one another along an optical axis of the apparatus along which the first and second lenses and the camera sensor are positioned such that the first lens forms an image of a retina of the eye at a location in between the first and second lenses and said at least a second lens relays the image of the retina onto the camera sensor;
a mechanism configured to change the locations of the first lens and of the light source relative to one another after the apparatus has been used to capture a first snapshot fundus image of the eye of the subject, wherein after the locations of the first lens and the light source relative to one another have been changed, the apparatus captures a second snapshot fundus image of the same eye of the same subject; and
a processor configured to perform a digital compensation algorithm that processes the first and second snapshot fundus images to create a third snapshot fundus image corresponding to one of the first and second snapshot fundus images with any reflection artifacts removed.

\* \* \* \* \*